United States Patent
Blank

(10) Patent No.: US 6,529,016 B1
(45) Date of Patent: Mar. 4, 2003

(54) APPARATUS MONITORING THE DEPOSITION OF A LIQUID-TO-PASTY MEDIUM ON A SUBSTRATE

(75) Inventor: Andreas Blank, Velbert (DE)

(73) Assignee: ITW Industrie GmbH, Mettmann (DE)

( * ) Notice: Subject to any disclaimer, the term of this patent is extended or adjusted under 35 U.S.C. 154(b) by 0 days.

(21) Appl. No.: 09/634,712

(22) Filed: Aug. 7, 2000

(30) Foreign Application Priority Data

Aug. 7, 1999 (DE) .......................................... 199 37 387

(51) Int. Cl.[7] .............................................. G01R 27/26
(52) U.S. Cl. ...................................... 324/690; 324/664
(58) Field of Search ............................... 324/452, 659, 324/664, 671, 690, 601

(56) References Cited

U.S. PATENT DOCUMENTS

| | | | |
|---|---|---|---|
| 3,766,469 A | 10/1973 | Nakane | 324/659 |
| 3,801,900 A | 4/1974 | Szasz | 324/671 |
| 4,288,741 A | 9/1981 | Dechene et al. | 324/664 |
| 4,471,295 A | 9/1984 | Vermeiren | |
| 5,001,435 A | 3/1991 | Smith | 324/671 |
| 5,585,732 A | * 12/1996 | Steele et al. | 324/663 |
| 5,760,589 A | 6/1998 | Katsuie | 324/452 |

FOREIGN PATENT DOCUMENTS

| | | |
|---|---|---|
| DE | 3143526 | 6/1982 |
| DE | 3832763 A1 | 4/1989 |
| DE | 4217736 | 12/1993 |
| DE | 42 17 736 C2 | 6/1999 |
| EP | 0 060 588 A1 | 9/1982 |
| GB | 1348982 | 3/1974 |

OTHER PUBLICATIONS

Microelectronic Circuit, Fourth edition, pp. 980–981, Published 1997. No month available.*
FH–Düsseldorf Labor Werkstofkunde. Frequenzgang der komplexen Permittivität. Prof. Dr.–Ing. Prochotta. Sep. 4, 1998.

* cited by examiner

Primary Examiner—N. Le
Assistant Examiner—Vincent Q. Nguyen
(74) Attorney, Agent, or Firm—Lowe Hauptman Gilman & Berner, LLP

(57) ABSTRACT

An apparatus for monitoring deposition of a liquid-to-pasty medium on a substrate has a sensor fitted with two electrodes and an electronic circuit connected to the sensor for generating a signal which is characteristic of the substrate and the medium. The electronic circuit measures the imaginary component of the electrical permittivity of the substrate moving, together with the medium, between the two electrodes, and uses the measured value to determine the characteristic signal.

4 Claims, 3 Drawing Sheets

APPARATUS MONITORING THE DEPOSITION OF A LIQUID-TO-PASTY MEDIUM ON A SUBSTRATE

TECHNICAL FIELD OF THE INVENTION

The invention relates to apparatus monitoring the deposition of a liquid-to-pasty medium on a substrate as defined in the preamble of claim 1.

BACKGROUND OF THE INVENTION

Such apparatus is described in the German patent document 4 217 736 C2. Therein each electrode is a sensor which is a component of a high-frequency oscillation circuit and as such detects a change in frequency when there is a change in the relative electric permittivity of the medium between the electrodes.

In this design the sensor is capacitive, that is it is inserted as a capacitor in the high-frequency oscillation circuit. Depending on the kind of medium between the two probes, that is, depending whether air is involved, or a substrate without a strip of glue or a substrate with a strip of glue of various thickness, the capacitance of such configuration will change. However the system capacitance strongly depends on the relative dielectric constant of the materials assuming much different values for air, glue and paper.

A typical change in system capacitance however also changes the frequency, allowing determining for instance whether the substrate comprises or not a strip of glue.

The know apparatus monitoring the deposition of a liquid-to-pasty medium on a substrate does its job well. However there may be malfunctions in some cases.

SUMMARY OF THE INVENTION

Based on the known apparatus of the German patent document 4 217 736 C2, it is the objective of the invention to create an apparatus that offers improved reliability and higher accuracy of measurement.

This problem is solved by the invention in accordance with which the apparatus measures the imaginary component of the permittivity of the substrate together with the medium between the two electrodes, the test electronics thereupon using this test value to determine the characteristic signal.

It is the insight of the invention that the permittivity, ie the dielectric constant, is a complex value, that is it comprises a real component and an imaginary component. Furthermore experiment has shown, with respect to the materials of significance herein, especially liquid-to-pasty glue such as is used in glue strips on cardboard, on paper mats or the like, that the imaginary components of the permittivity are larger, sometimes even by an order of magnitude, than the real components.

Based on such empirical findings, the invention concludes that, considering the numerically larger value of the imaginary component of the permittivity, measuring this imaginary component shall be simpler and more reliable when determining the nature of the tested material.

Derivation of the pertinent formulas is briefly discussed below. Further details can be found in the article "Frequenz-Zugang der komplexen Permittivität", FH Duesseldorf [Germany] Labor Werkstoffkunde, Sep. 4, 1998, pp 1–14.

The individual microscopic effects noted when a dielectric material is situated in an alternating electric field are best stated by a complex permittivity $$\epsilon_r = \epsilon_r' - j\epsilon_r''.$$

where $\epsilon_r'$ is the real component and $\epsilon_r''$ is the imaginary component of the permittivity $\epsilon_r$.

The particular microscopic phenomena affecting this value will be not be elucidated herein. Basically, they involve effects of alignment, ionic and electronic polarizations. The permittivity, and both its components, are strongly frequency-dependent.

The term $\epsilon_r''$ describes the dielectric losses and accordingly it is a measure of the energy absorbed by the glue.

These dielectric losses behave like ohmic heat losses. This fact can be expressed also by the so-called loss tangent $$\tan \delta = \epsilon_r''/\epsilon_r'.$$

FIGS. 1 and 2 illustrate this matter. FIG. 1 schematically shows the equivalent circuit of an actual lossy capacitor. When applying an AC voltage U, a current I is set up in the capacitor. This current comprises two parts, namely the current $I_c$ which would be set up in ideal capacitor, and parallel thereto the loss current Iv through a resistor, representing the dielectric losses as heat in the capacitor.

FIG. 2 is a diagram of the two components, namely lossy current and current through the idealized capacitor, which when added represent the total current I through the actual capacitor.

It follows from the equivalent circuit, $$Y = G + j\omega C,$$

where Y is the admittance, G the dissipative conductance and $j\omega C$ the reactive admittance in the loss-free capacitor.

In the event that a test object be present in the capacitor, $$Y = j\omega * C_{material}.$$

The capacitance of a parallel plate capacitor is given by the formula $$C = \epsilon_o \epsilon_r A/d$$

where A is the surface of each plate of a parallel plate capacitor and d is the distance between these plates, $\epsilon_r$ being the relative dielectric constant of the material.

The latter two formulas directly lead to $$Y = j\omega * (\epsilon_r' - j\epsilon_r'') * \epsilon_o A/d.$$

Using herebelow $$C_o = \epsilon_o A/d$$

then $$G + j\omega * C = j\omega * (\epsilon_r' - j\epsilon_r'') + C_o$$

$$G + j\omega * C = \omega * \epsilon_r'' * C_o + j\omega * \epsilon_r' * C_o$$

whence $$C = \epsilon_r' * C_o.$$

However this indicates that only the real component of the permittivity accounts for the capacitance. Accordingly the heretofore conventional capacitance measurements will not detect the permittivity's complex component.

Attention is now drawn to Tables 1 and 2 below.

TABLE 1

| | | | | | | | |
|---|---|---|---|---|---|---|---|
| C_r/pF | 1.4 | | | | | | |
| C_s/pF | 0.2 | | | | | | |
| f/MHZ | 0.075 | 0.1 | 0.15 | 0.2 | 0.3 | 0.5 | 1 |
| C/pF | 100.28 | 99.80 | 99.17 | 98.74 | 98.16 | 96.44 | 96.41 |
| C_k/pF | 99.48 | 98.0 | 97.37 | 96.94 | 96.94 | 95.64 | 94.61 |
| G/μs | 1.38 | 1.74 | 2.43 | 3.10 | 4.42 | 7.03 | 13.18 |
| C_L/pF | 18.93 | 18.93 | 18.93 | 18.92 | 18.82 | 18.92 | 18.92 |
| C_LN/pF | 17.13 | 17.13 | 17.13 | 17.12 | 17.12 | 17.12 | 17.12 |
| ∈_r' | 5.68 | 5.72 | 5.68 | 5.66 | 5.63 | 5.58 | 5.52 |
| ∈_r" | 0.17 | 0.16 | 0.15 | 0.14 | 0.14 | 0.13 | 0.12 |
| tan δ | 0.03 | 0.028 | 0.026 | 0.025 | 0.025 | 0.023 | 0.022 |

TABLE 2

| | | | | | | | |
|---|---|---|---|---|---|---|---|
| C_r/pF | 1.4 | | | | | | |
| C_s/pF | 0.2 | | | | | | |
| f/MHZ | 0.075 | 0.1 | 0.15 | 0.2 | 0.3 | 0.5 | 1 |
| C/pF | 1187 | 965 | 879 | 653 | 548 | 459 | 381 |
| C_k/pF | 1185.4 | 963.4 | 877.4 | 651.4 | 546.4 | 457.4 | 379.4 |
| G/μs | 4,074 | 4,163 | 4,293 | 4,374 | 4,447 | 4,620 | 4,935 |
| C_L/pF | 16.55 | 16.55 | 16.55 | 16.54 | 16.54 | 16.54 | 16.54 |
| C_LN/pF | 14.95 | 1495 | 14.95 | 14.94 | 14.94 | 14.94 | 14.94 |
| ∈_r' | 79.3 | 64.44 | 58.7 | 43.6 | 36.6 | 30.6 | 25.4 |
| ∈_r" | 578.3 | 443.2 | 304.7 | 233.0 | 157.9 | 98.4 | 52.6 |
| tan δ | 7.29 | 6.88 | 5.19 | 5.34 | 4.31 | 3.22 | 2.07 |

Table 1 shows a number of test values for paper inserted between the plates of a parallel plate capacitor. Table 2 shows the corresponding test values for the dielectric between the capacitor's plates consisting of two paper layers sandwiching glue layers.

The notation used in these Tables is as follows: $C_r$ is the capacitance portion of the tested sample's capacitance taking into account the edge field of the parallel plate capacitor; CS is the capacitance portion taking into account the stray field to ground; f is the applied frequency, C is the measured capacitance, $C_k$ is the corrected measured capacitance, $C_{LK}$ is the corrected capacitance of the test system without a test sample, G is the admittance of the dielectric, $C_L$ is the capacitance of the test system without a test sample, $\in_r'$ is the real component of the permittivity, $\in_r''$ is the imaginary component of the permittivity, and tan δ is the loss factor.

Further information also can be found in the aforementioned article by J Prochetta PhD.

It is immediately clear from the Tables that when the dielectric is glue, the absolute values of the imaginary component $\in_r''$ of the permittivity are order(s) of magnitude larger than the real component $\in_r'$. Consequently measuring this imaginary component of the permittivity will be far more revelatory about the dielectric situated between the two electrodes. This is the heart of the invention.

It is furthermore clear from the above that the ratio of glue $\in_r''$ to paper $\in_r''$ is more than two orders of magnitude larger than the ratio of glue $\in_r'$ to paper $\in_r'$.

In an advantageous implementation of the invention, the imaginary permittivity component is measured by testing the current, or a current drop, through the substrate. This procedure takes into account that when measuring the current, the dielectric's imaginary permittivity component is especially easy to measure. From the above formulas, it follows $$G = \omega * \in_r'' * C_o.$$

This formula shows that the loss portion G is directly proportional to the imaginary permittivity component. Therefore measuring this lossy current at once provides the desired result.

In a further advantageous implementation of the invention, the measurement of the current or of the current drop is carried out using a current-controlled voltage amplifier, in particular using a current-to-voltage (I-U) converter. As a result minute currents can be measured in simple and advantageous manner.

In another advantageous design, the current-to-voltage converter is connected to an adder in turn connected to the output of a first operational amplifier. This configuration allows advantageous and simple further processing of the detected signal at the output of said current-to-voltage converter.

In another embodiment of the invention, a first phase shifter is mounted between the input of the first operational amplifier and an AC voltage source. The function of this first phase shifter is to compensate the current-voltage shift at the output of the current-to-voltage (I-U) converter.

In a further advantageous embodiment of the invention, the phase-shifter is phase-inverting. In this manner the apparatus can be adjusted in such a way that when adjusting an empty sensor, that is without substrate and without medium, the test result at the adder's output shall be 0. In this manner the minute tested voltages can be advantageously processed when a dielectric shall be situated between the electrodes.

In a further advantageous embodiment of the invention, the current-to-voltage converter comprises a circuit having a third operational amplifier. This feature allows economic and simple manufacture of the current-to-voltage converter.

In a further advantageous embodiment of the invention, a first input of the third operational amplifier—in particular the inverting input—is connected directly to one of the sensor electrodes. In this manner a signal can be detected without fear of interference.

In a further advantageous embodiment of the invention, the two electrodes are mounted on different sides of the substrate. This configuration is like a parallel plate capacitor with two planar electrodes between which the substrate—with or without medium—shall be moved. Furthermore this design allows measuring through the substrate and through the medium transversely to the plane of the substrate. This procedure makes possible very simple measurements.

Another alternative design is to configure the two electrodes on one side of the substrate. In this case the imaginary component of the permittivity also takes place between the electrodes, this time at least partly in a plane which is parallel to that of the substrate surface.

BRIEF DESCRIPTION OF THE DRAWINGS

Further advantages of the invention are achieve in illustrative embodiments shown in the attached Figures.

DETAILED DESCRIPTION OF THE INVENTION

Figure 1:
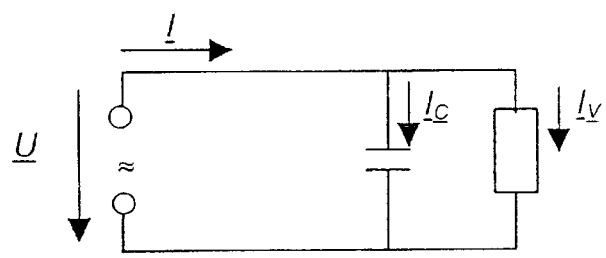
FIG. 1 is the equivalent circuit or a practical, dissipative capacitor.
Figure 2:
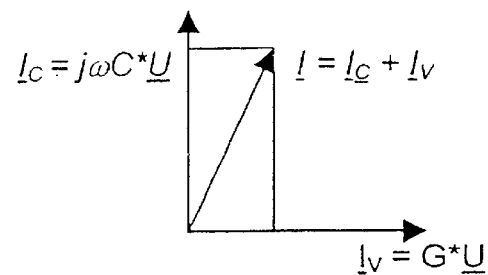
FIG. 2 is the current diagram illustrating the two current components shown in the equivalent circuit of FIG. 1.
Figure 4:
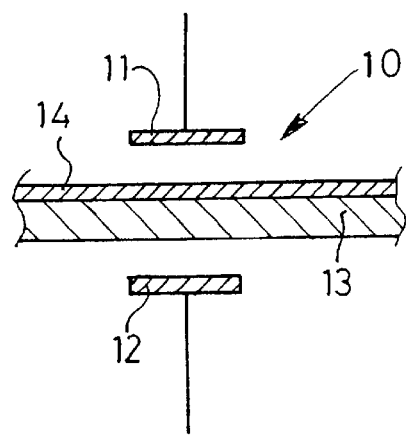

The apparatus monitoring the deposition of a liquid-to-pasty medium on a substrate is only partly shown herein; in the manner of the invention, it comprises a sensor 10 which is shown merely schematically in FIG. 4. In the embodiment of FIG. 4, this sensor 10 basically is a parallel plate capacitor of which the two electrodes 11 and 12 are essentially planar. A length of material 13 is situated between the two electrodes 11, 12 of FIG. 4 and glue 14 is deposited on said length on its side facing the upper electrode 11.

Reference is made in general manner to the German patent documents 4 217 736 C2 and 3 934 852 C2 regarding the general design, operation and related problems of glue-deposition monitoring apparatus.

The apparatus of the invention differs from those described in the above two documents essentially by the kind of sensors used and by the measurement techniques, ie the test electronics.

The apparatus of the invention furthermore shall monitor the deposition of a medium, in particular glue, in order to determine, along a manufacturing line, appropriate glue strips on cardboard items, on diapers made of this plastic foils and non-wovens, or the like, or, to emit an alarm or the like in the case of inappropriate glue strips.

Figure 3:
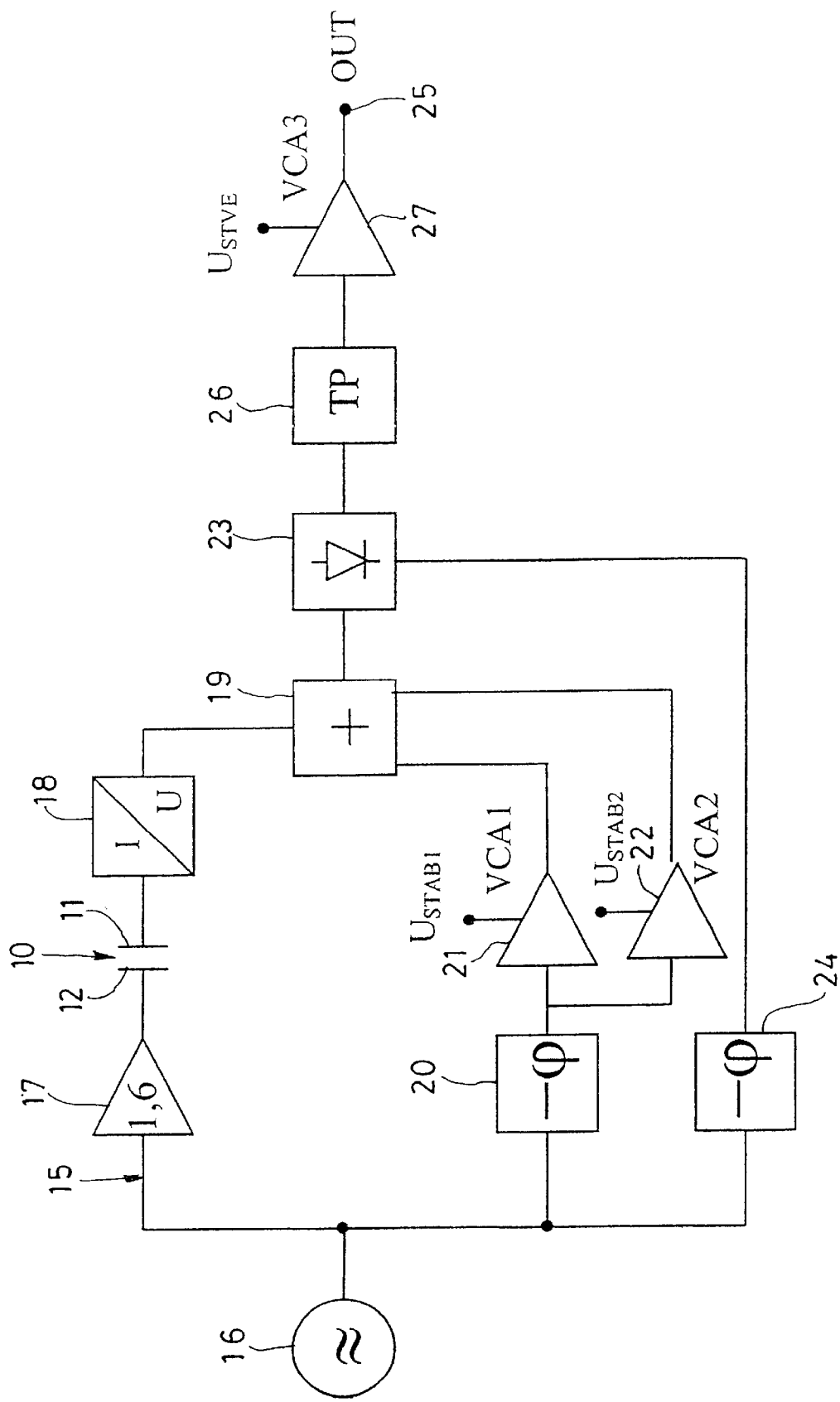
FIG. 3 is the functional block diagram of a test electronics used in the apparatus of the invention, FIG. 4 diagrammatically shows the region of a sensor comprising two planar electrodes and with length of material sandwiched between said electrodes.
Figure 5:
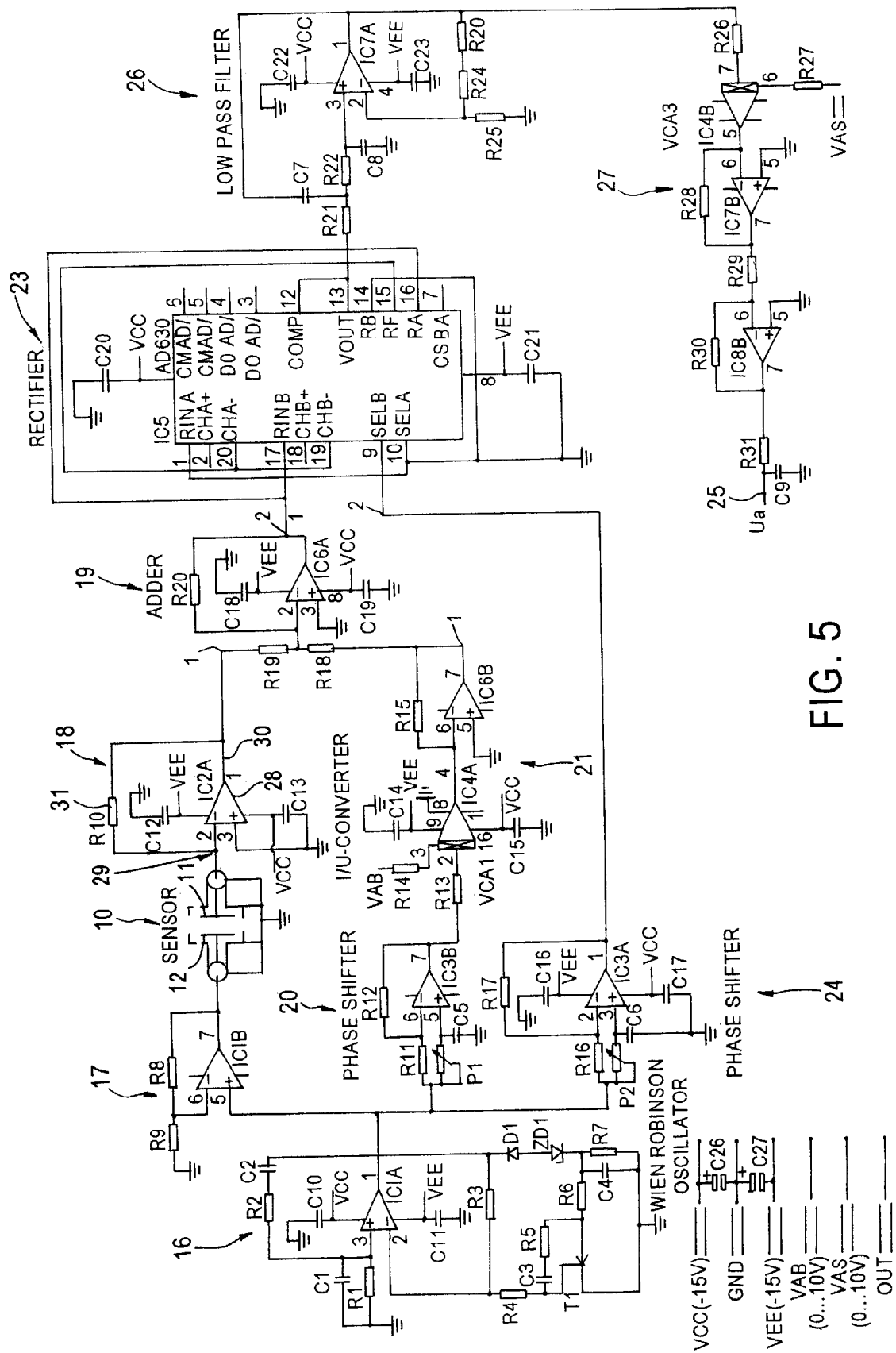
FIG. 5 is a comprehensive circuit diagram of the test electronics of FIG. 3.

As shown in FIG. 3, the sensor 10, which is also called a sensor fork, is inserted into a test circuit denoted overall by the reference 15. This test circuit comprises an AC voltage source 16 which in the embodiment of FIGS. 3 and 5 is designed as a Wien-Robinson oscillator.

This oscillator first is connected to an amplifier 17 illustratively having a gain of 1.6, the AC voltage signal then being applied to the first electrode 12, i.e. the lower one in FIG. 4. The opposite electrode 11 of the embodiment of FIG. 4, i.e. the upper one, is connected directly to a current-to-voltage (I-U) converter 18 (FIG. 3). Said converter measures the dissipation current in the sensor 10.

The output of the I-U converter 18 is connected to an adder 19.

A second conductor from the AC voltage source 16 runs to a first and inverting phase-shifter 20. The output of said phase shifter is connected to the input of a first operational amplifier 21. The output of the first operational amplifier 21 runs to the input of the adder 19.

The purpose of the circuit branch described just above is to use the first phase shifter 20 to match the sinusoidal AC voltage to the phase-shifted output of the I-U converter 18.

By adding the output values from the first operational amplifier 21 and from the I-U converter 18, the test value, namely that of the dissipative current in the sensor 10, already have been ascertained in principle.

However to carry out such measurement in more elegant form, a further configuration is used, namely the output of the first phase shifter 20 is connected to the input of a second operational amplifier 22. In turn this output is also connected to the adder 19. The significance of this branching is elucidated further below.

Moreover the output of the adder 19 is connected to a rectifier 23. A second, inverting phase shifter 24 is branched separately between the rectifier 23 and the AC source 16.

The last two cited branches cooperate as follows: the AC voltage beyond the adder 19, that is, at the output of the adder 19, can be matched by means of the second phase shifter 24 in such a way that a positive DC always shall be present at the output of the rectifier 23. This feature obviously is advantageous in the subsequent signal processing.

A lowpass filter 26 is present between the rectifier 23 and the output 25 of the test electronics 15. Said lowpass filter also offers known basic advantages in testing.

Lastly a fourth operational amplifier of the output signal is used.

FIG. 5 shows the test electronics of FIG. 3 in detail. Identical components or functional blocks are denoted by the same references. However the second operational amplifier 22 shown in FIG. 3 is absent, not being basically required.

FIG. 5 shows the details of the current-to-voltage converter 18, which substantially comprises an operational amplifier 28.

In this manner a conventional commercial component such as LF412 may be used, which is also applicable in the remaining components such as the phase shifters 20, 24, the first operational amplifier 21, the fourth operational amplifier 27, the adder 19, the lowpass filter 26, and also in the AC voltage source 16.

The capacitances and resistances listed in this circuit are substantially appropriate; It is understood however that the particular listings are merely illustrative.

A 1-megohm resistance 31 runs across the inverting input 29 of the third operational amplifier 28 and its output 30.

The electrodes 11, 12 of the sensor 10 of the discussed embodiment are in the form of the plates of a parallel plate capacitor. However the concept of the invention is not restricted to such geometries. In principle any electrode geometry is applicable to measure the imaginary component of the permittivity.

A phase shift from 0 to 170° can be set at the phase shifters. This feature substantially is only used to adjust the output values. The control voltages USTAB1 and USTAB2 applied to the first and second operational amplifiers 21 and 22 (FIG. 3) are used for the same purpose. The balancing is undertaken in the absence of a dielectric between the electrodes. The control voltages are continuously adjustable between 0 and 10 v.

Illustratively the applied test frequency will be 100 kHz. However frequencies in the range from a few kHz to several tens or hundreds of MHZ also might be used. The particular frequency depends on the liquid-to-pasty medium to be deposited. Depending on the kind of glue, the values of the imaginary permittivity component or the ratio of imaginary to real permittivity components may vary. As a rule however, a frequency once set will remain constant during monitoring.

The amplifier 17 shown in FIGS. 3 and 5 is merely optional. However it was found to be advantageous.

What is claimed is:

1. A device for monitoring deposition of a medium on a substrate, said device comprising:
    a device input and a device output, said device input being connectable to an AC voltage source;
    a first electrode connected to said device input;
    a second electrode physically spaced from said first electrode by a distance sufficient to allow the substrate carrying the medium to pass between said electrodes, said first and second electrodes being electrically isolated from each other thereby forming a sensing capacitor; and
    a measuring circuit electrically connected to said second electrode and said device output, said circuit measuring the imaginary component of an electrical permittivity of the substrate and the medium situated between said electrodes, and generating, at said device output, a signal corresponding to the measured electrical permittivity;

wherein
said circuit comprises a current-to-voltage converter having an input connected to said second electrode;
said circuit further comprises an adder and a first operational amplifier;
the current-to-voltage converter further has an output connected to an input of the adder which in turn is connected to an output of the first operational amplifier;
said circuit further comprises a first phase shifter having an input connected to said device input and an output connected to an input of the first operational amplifier; and
said circuit further comprises a second operational amplifier having an input connected to the output of the first phase shifter and an output connected to the input of the adder.

2. A device for monitoring deposition of a medium on a substrate, said device comprising:

a device input and a device output, said device input being connectable to an AC voltage source;

a first electrode connected to said device input;

a second electrode physically spaced from said first electrode by a distance sufficient to allow the substrate carrying the medium to pass between said electrodes, said first and second electrodes being electrically isolated from each other thereby forming a sensoring capacitor; and a measuring circuit electrically connected to said second electrode and said device output, said circuit measuring the imaginary component of an electrical permittivity of the substrate and the medium situated between said electrodes, and generating, at said device output, a signal corresponding to the measured electrical permittivity;

wherein
said circuit comprises a current-to-voltage converter having an input connected to said second electrode;
said circuit further comprises an adder and a first operational amplifier;
the current-to-voltage converter further has an output connected to an input of the adder which in turn is connected to an output of the first operational amplifier;
said circuit further comprises a rectifier having an input connected to an output of the adder and an output connected to said device output; and
said circuit further comprises a second phase shifter having an input connected to said device input and an output connected to another input of the rectifier.

3. In combination, a substrate and a device for monitoring deposition of a liquid-to-pasty medium on the substrate, said device comprising:

a device input and a device output, said device input being connectable to an AC voltage source;

a fist electrode connected to said device input;

a second electrode physically spaced from said first electrode by a distance sufficient to allow the substrate to pass between said electrodes, said first and second electrodes being electrically isolated from each other thereby forming a sensoring capacitor, the substrate continuously moving in spaced relationship with respect to said electrodes; and a measuring circuit electrically connected to said second electrode and said device output, said circuit measuring the imaginary component of an electrical permittivity of a portion of the substrate which is currently situated between said electrodes, said circuit further generating, at said device output, a signal corresponding to the measured electrical permittivity;

wherein
said circuit comprises a current-to-voltage converter having an input connected to said second electrode;
said circuit further comprises an adder and a first operational amplifier;
the current-to-voltage converter further has an output connected to an input of the adder which in turn is connected to an output of the first operational amplifier;
said circuit further comprises a first phase shifter having an input connected to said device input and an output connected to an input of the first operational amplifier; and
said circuit further comprises a second operational amplifier having an input connected to the output of the first phase shifter and an output connected to the input of the adder.

4. In combination, a substrate and a device for monitoring deposition of a liquid-to-pasty medium on the substrate, said device comprising:

a device input and a device output, said device input being connectable to an AC voltage source;

a first electrode connected to said device input;

a second electrode physically spaced from said first electrode by a distance sufficient to allow the substrate to pass between said electrodes, said first and second electrodes being electrically isolated from each other thereby forming a sensoring capacitor, the substrate continuously moving in spaced relationship with respect to said electrodes; and a measuring circuit electrically connected to said second electrode and said device output, said circuit measuring the imaginary component of an electrical permittivity of a portion of the substrate which is currently situated between said electrodes, said circuit generating, at said device output, a signal corresponding to the measured electrical permittivity;

wherein
said circuit comprises a current-to-voltage converter having an input connected to said second electrode;
said circuit further comprises an adder and a first operational amplifier;
the current-to-voltage converter further has an output connected to an input of the adder which in turn is connected to an output of the first operational amplifier;
said circuit further comprises a first phase shifter having an input connected to said device input and an output connected to an input of the first operational amplifier;
said circuit further comprises a rectifier having an input connected to an output of the adder and an output connected to said device output; and
said circuit further comprises a second phase shifter having an input connected to said device input and an output connected to another input of the rectifier.

* * * * *